United States Patent
Lazarowitz

(10) Patent No.: US 6,248,792 B1
(45) Date of Patent: Jun. 19, 2001

(54) USE OF CARBOXYLATE ALKYL POLYGLYCOSIDE SURFACTANT TO INCREASE THE FOAM OF OTHER ANIONIC SURFACTANTS

(75) Inventor: Virginia Lazarowitz, Hatfield, PA (US)

(73) Assignee: Henkel Corporation, Gulph Mills, PA (US)

( * ) Notice: Subject to any disclaimer, the term of this patent is extended or adjusted under 35 U.S.C. 154(b) by 0 days.

(21) Appl. No.: 09/323,797

(22) Filed: Jun. 1, 1999

(51) Int. Cl.[7] ............... B01F 3/04; B01F 17/00; C09K 3/00; A61K 7/50; C11D 7/50
(52) U.S. Cl. ............... 516/14; 516/10; 516/19; 510/135
(58) Field of Search ............... 516/10, 14, 19; 510/135

(56) References Cited

U.S. PATENT DOCUMENTS

| | | | |
|---|---|---|---|
| 4,565,647 | * 1/1986 | Llenado | 252/354 |
| 4,806,275 | * 2/1989 | Johnson et al. | 252/554 |
| 5,207,932 | * 5/1993 | Norman et al. | 252/3 |
| 5,908,928 | * 6/1999 | Milstein et al. | 536/120 |
| 5,962,399 | * 10/1999 | Wulff et al. | 510/470 |

* cited by examiner

Primary Examiner—Jill Warden
Assistant Examiner—Monique T. Cole
(74) Attorney, Agent, or Firm—John E. Drach; Joanne M. Rossi; Steven J. Trzaska

(57) ABSTRACT

The present invention relates to the use of a carboxylated alkyl polyglycoside in combination with an anionic surfactant to increase foam. The carboxylated alkyl polyglycoside, according to the invention, can be the reaction product of an alkyl polyglycoside with an alpha- or 2-halocarboxylic acid; the reaction product of an alkyl polyglycoside with an alpha, beta-unsaturated carboxylic acid; or the reaction product of an alkyl polyglycoside with a cyclic carboxylic acid anhydride.

16 Claims, 8 Drawing Sheets

FIG. I

USE OF CARBOXYLATE ALKYL POLYGLYCOSIDE SURFACTANT TO INCREASE THE FOAM OF OTHER ANIONIC SURFACTANTS

FIELD OF THE INVENTION

The present invention generally relates to the use of carboxylated alkyl polyglycosides in conjunction with other anionic surfactants to increase foam.

BACKGROUND OF THE INVENTION

It is known that various surfactants have been found to be useful in cleaning compositions, such as shower gels, shampoos, and light-duty detergents such as dish washing detergents and fine fabric wash. In these types of compositions, good foamability is a prerequisite. The most widely used surfactants in these types of compositions are anionic surfactants such as alkyl sulfates, alkyl ether sulfates, sulfonates, sulfosuccinates and sarcosinates.

Although the use of anionic surfactants in these compositions permits the attainment of desirable properties, including good foamability, the degree of foam stability leaves much to be desired. Foam stability relates to the ability of the foam, once formed, to remain intact for extended periods of time, thus enhancing the cleaning performance of the surfactant compositions.

It is sometimes advantageous to use mixtures of surfactants in cleaning compositions when the surfactants can serve different functions, e.g., one serving to improve foamability and another serving to adjust viscosity. However, known surfactant mixtures typically provide a compromise between what can be achieved with the surfactant ingredients alone. For example, a mixture of more costly surfactants such as amine oxides, betaines and alkanolamides which provide good foamability by themselves, with less expensive surfactants which provide poorer foamability will result in the formulation of a cleaning composition having an intermediate degree of foamability and poor foam stability.

Alkyl polyglycosides are used as nonionic surfactants and are distinguished from other nonionic surfactants by their excellent detergent properties and high ecotoxicological compatibility. They are generally used in liquid formulations, for example, dishwashing detergents and hair shampoos. However, because of their increased desirability as surface active agents, their use as surfactants in many other types of products is growing rapidly. The desire to further improve the characteristics of the alkyl polyglycosides has led to the carboxylated alkyl polyglycoside surfactants. These new anionic carboxylated alkyl polyglycosides have shown improved beneficial properties and uses as compared to the nonionic alkyl polyglycosides.

SUMMARY OF THE INVENTION

The present invention relates to the use of a carboxylated alkyl polyglycoside in combination with an anionic surfactant to increase foam. The carboxylated alkyl polyglycoside, according to the invention, can be the reaction product of an alkyl polyglycoside with an alpha- or 2-halocarboxylic acid; the reaction product of an alkyl polyglycoside with an alpha, beta-unsaturated carboxylic acid; or the reaction product of an alkyl polyglycoside with a cyclic carboxylic acid anhydride.

Particularly preferred carboxylated alkyl polyglycosides have the general formula I:

$$R_1O(R_2O)_b(Z)_aOCH_2COO^-X^+ \quad \text{(I)}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6; and X is an alkali metal ion.

DESCRIPTION OF THE INVENTION

Figure 1:
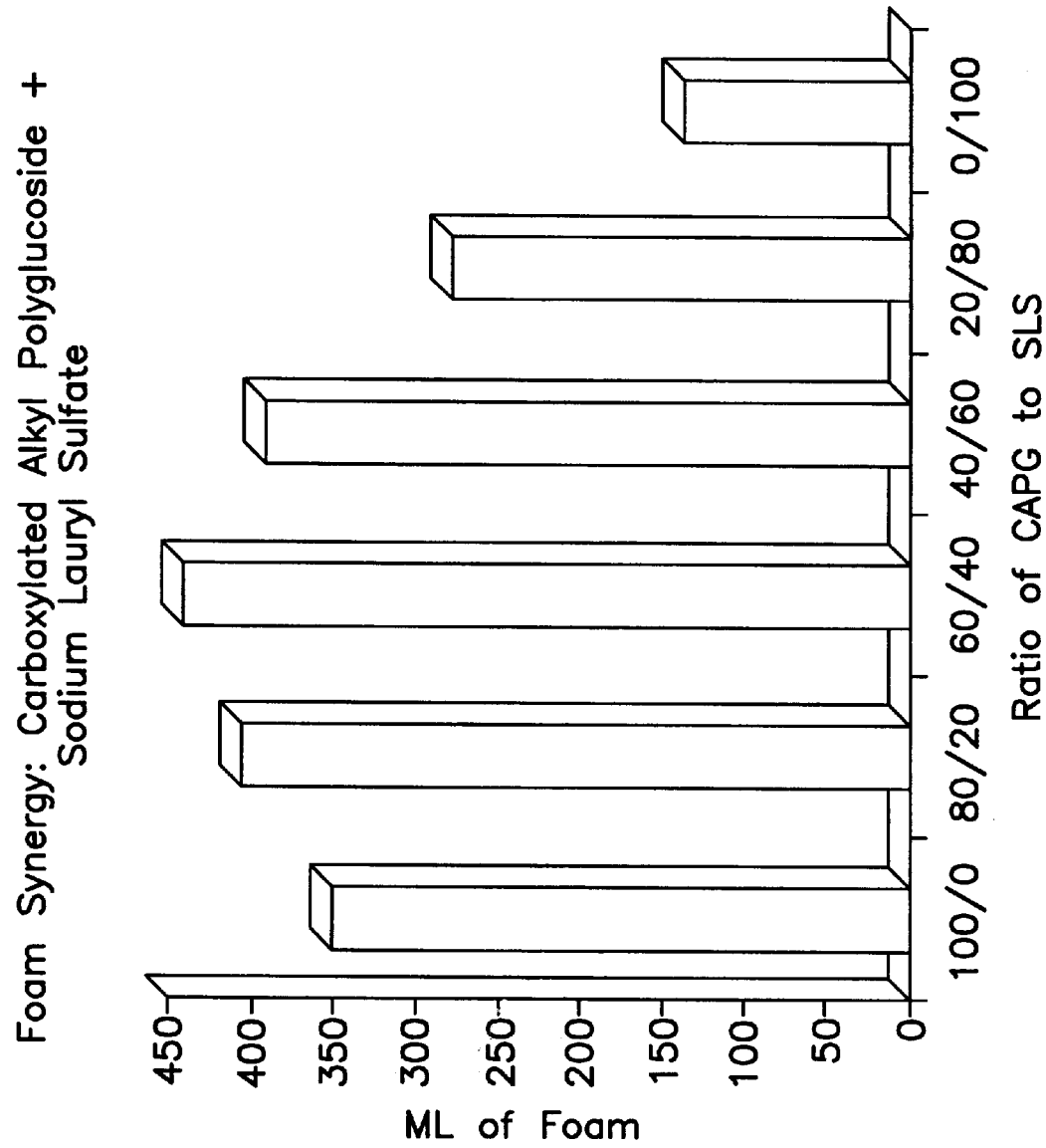
FIG. 1: Foam synergy of a carboxylated alkyl polyglycoside surfactant (CAPG) with sodium lauryl sulfate (SLS).
Figure 2:
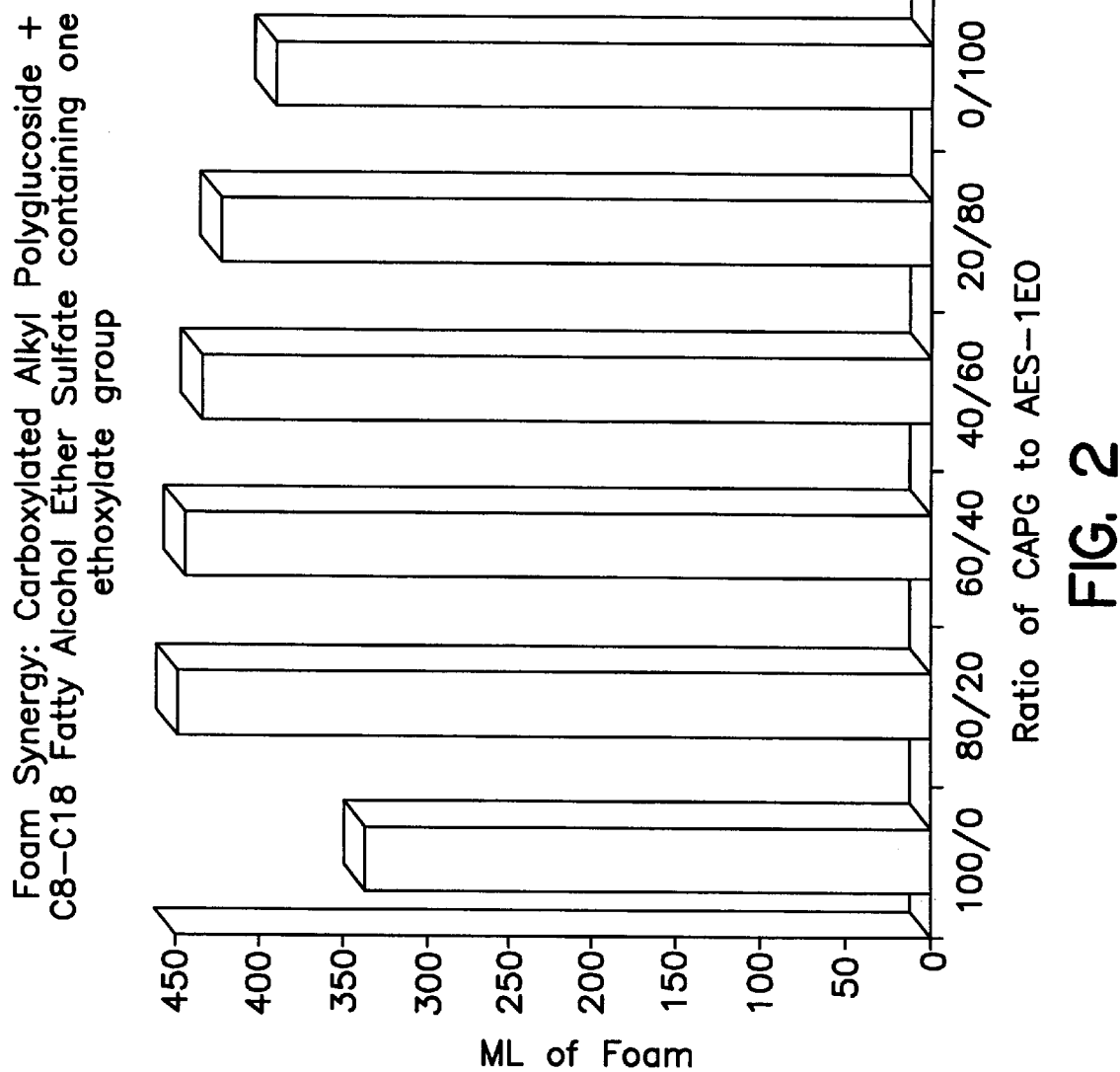
FIG. 2: Foam synergy of a carboxylated alkyl polyglycoside surfactant (CAPG) with a C8–18 fatty alcohol ether sulfate containing one ethoxylate group (AES-1EO).
Figure 3:
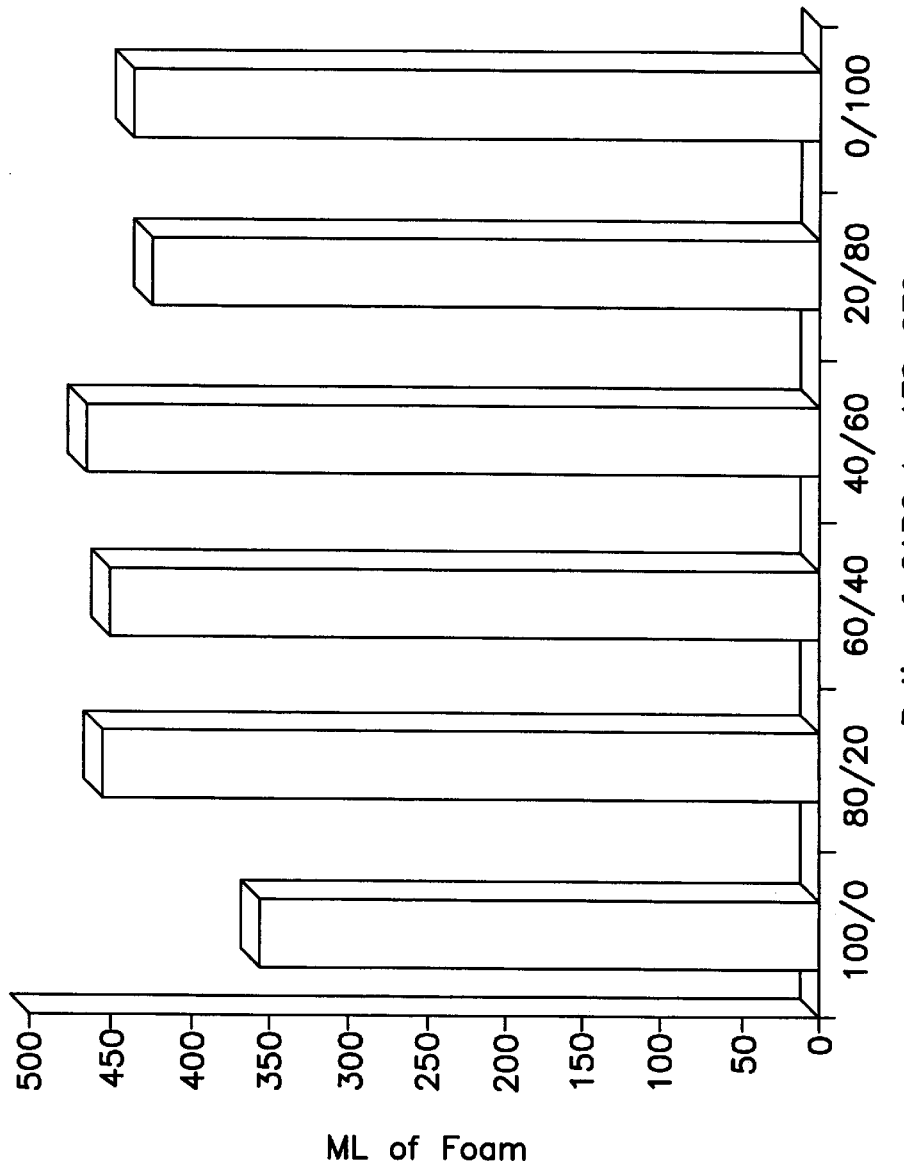
FIG. 3: Foam synergy of a carboxylated alkyl polyglycoside surfactant (CAPG) with a C8–18 fatty alcohol ether sulfate containing two ethoxylate groups (AES-2EO).
Figure 4:
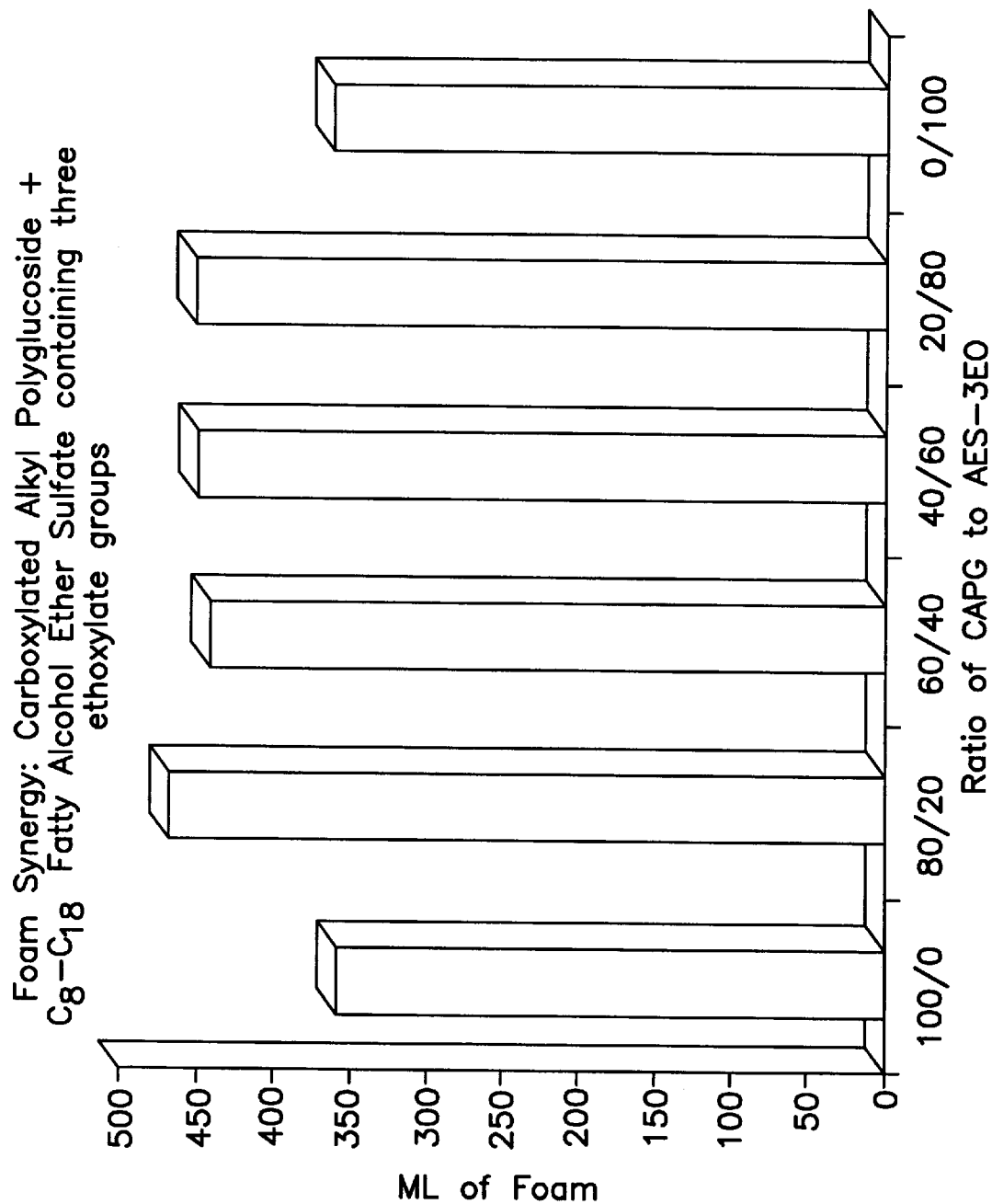
FIG. 4: Foam synergy of a carboxylated alkyl polyglycoside surfactant (CAPG) with a C8–18 fatty alcohol ether sulfate containing three ethoxylate groups (AES-3EO).
Figure 5:
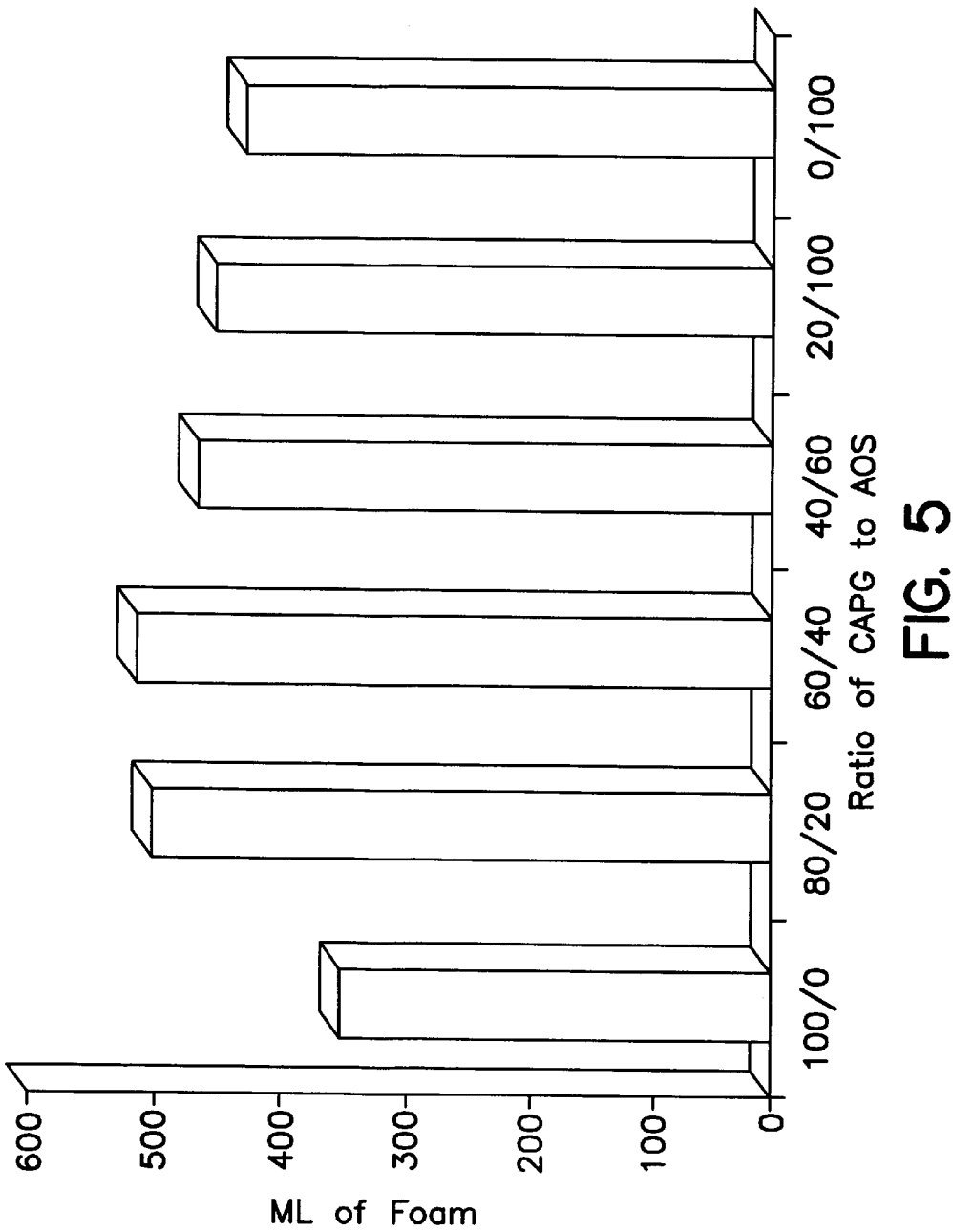
FIG. 5: Foam synergy of a carboxylated alkyl polyglycoside surfactant (CAPG) with a C10–18 fatty alcohol alpha olefin sulfonate (AOS).
Figure 6:
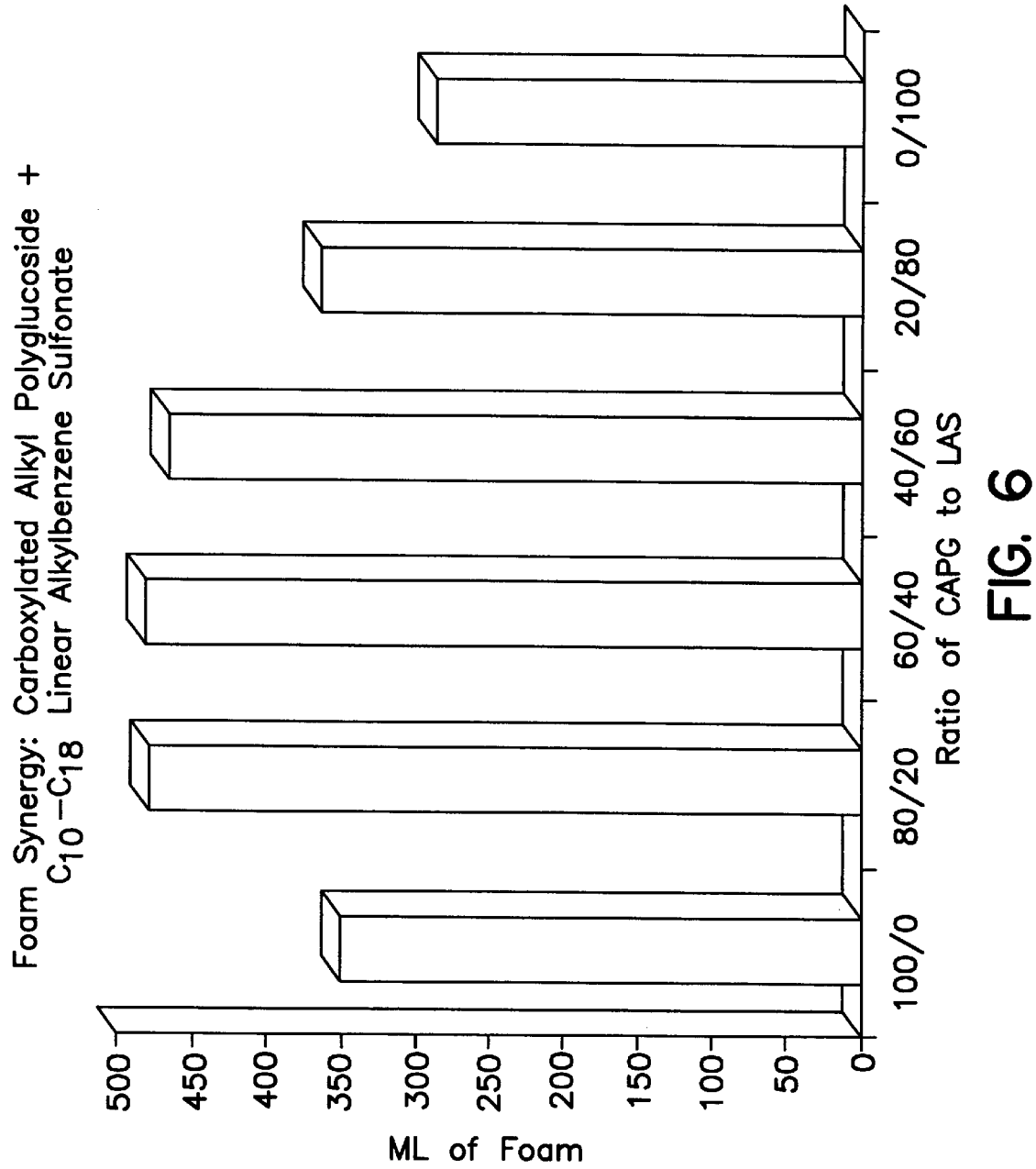
FIG. 6: Foam synergy of a carboxylated alkyl polyglycoside surfactant (CAPG) with a C10–18 linear alkylbenzene sulfonate (LAS).

Other than in the operating examples, or where otherwise indicated, all numbers expressing quantities of ingredients or reaction conditions are to be understood as being modified in all instances by the term "about".

It has surprisingly been discovered that the combination of an anionic surfactant and a carboxylated alkyl polyglycoside surfactant results in a foam synergy where the amount of foam for a given concentration of total surfactant is greater for the mixture of surfactants than for either the anionic surfactant or the carboxylated alkyl polyglycoside surfactant.

According to one aspect of the invention, there is provided a method of increasing the foam of an anionic surfactant comprising the step of mixing an anionic surfactant with a carboxylated alkyl polyglycoside surfactant having general formula I:

$$R_1O(R_2O)_b(Z)_aOCH_2COO^-X^+ \quad \text{(I)}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from about 1 to about 6 and preferably from about 1 to about 2; and X is an alkali metal ion.

The carboxylated alkyl polyglycoside surfactants possess anionic properties. They provide superior levels of stable foam and act as viscosity builders when used in various types of detergent compositions.

A variety of carboxylated alkyl polyglycoside surfactants can be used in the process according to the invention. The carboxylated alkyl polyglycosides can be made by such methods as the reaction of an alkyl polyglycoside with an alpha- or 2-halocarboxylic acid such as 2-chloroacetic acid as described in application Ser. No. 09/013,384 filed Jan. 26, 1998, the entire contents of which are herein incorporated by reference; or by the reaction of an alkyl polyglycoside with an alpha, beta-unsaturated carboxylic acid such as acrylic acid or methacrylic acid; or by the reaction of an alkyl polyglycoside with a cyclic carboxylic acid anhydride such as succinic anhydride or maleic anhydride. The carboxylated alkyl polyglycoside, according to the invention, can therefore be the reaction product of an alkyl polyglycoside with an alpha- or 2-halocarboxylic acid; the reaction product of an alkyl polyglycoside with an alpha, beta-unsaturated carboxylic acid; or the reaction product of an alkyl polyglycoside with a cyclic carboxylic acid anhydride.

Particularly preferred carboxylated alkyl polyglycoside surfactants are those of formula I where $R_1$ is a monovalent organic radical having from 8 to 16 carbon atoms, Z is a glucose residue, a is from about 1 to about 2 and a is preferably from about 1.4 to about 1.6 and b is zero. Particular examples of the carboxylated alkyl polyglycoside surfactants are those of formula I where $R_1$ is a monovalent organic radical having from 8 to 16 carbon atoms, Z is a glucose residue, a is about 1.55 and b is zero; $R_1$ is a monovalent organic radical having from 12 to 16 carbon atoms, Z is a glucose residue, a is about 1.6 and b is zero; $R_1$ is a monovalent organic radical having from 9 to 11 carbon atoms, Z is a glucose residue, a is about 1.6 and b is zero; $R_1$ is a monovalent organic radical having from 12 to 16 carbon atoms, Z is a glucose residue, a is about 1.4 and b is zero; $R_1$ is a monovalent organic radical having from 8 to 16 carbon atoms, Z is a glucose residue, a is about 1.5 and b is zero; $R_1$ is a monovalent organic radical having from 12 to 16 carbon atoms, Z is a glucose residue, a is about 1.6 and b is zero; $R_1$ is a monovalent organic radical having from 12 to 16 carbon atoms, Z is a glucose residue, a is about 1.4 and b is zero.

According to the invention a carboxylated alkyl polyglycoside surfactant is mixed with anionic surfactant to product a mixture that provides greater foaming then either the anionic or the carboxylated alkyl polyglycoside surfactant alone. Any anionic surfactant is suitable for use in the present invention. Anionic surfactants are broadly described as surface active compounds having one or more negatively charged functional groups. Included in this category is a C8–C22 alkyl fatty acid salt of an alkali metal, alkaline earth metal, ammonium, alkyl substituted ammonium, for example, isopropylamine salt, or alkanolammonium salt, for example, mono-, di-, or tri-ethanolamine salts. Sodium salts of tallow and coconut fatty acids and mixtures thereof are most common. Another important class of anionic compounds are the water-soluble salts, particularly the alkali metal salts, of organic sulfur reaction products having in their molecular structure an alkyl radical containing from about 8 to 22 carbon atoms and a radical selected from the group consisting of sulfonic and sulfuric acid ester radicals. Organic sulfur based anionic surfactants include the salts of C10–C16 alkylbenzene sulfonates, C10–C22 alkane sulfonates, C10–C22 alkyl ether sulfates, C10–C22 alkyl sulfates, C4–C10 dialkylsulfosuccinates, C10–C22 acyl isothionates, alkyl diphenyloxide sulfonates, alkyl naphthalene sulfonates, and 2-acetamido hexadecane sulfonates. Organic phosphate based anionic surfactants include organic phosphate esters such as complex mono- or diester phosphates of hydroxyl-terminated alkoxide condensates, or salts thereof. Included in the organic phosphate esters are phosphate ester derivatives of polyoxyalkylated alkylaryl phosphate esters, of ethoxylated linear alcohols and ethoxylates of phenol. A list of commercially available anionic surfactants can be found in McCutcheon's, Emulsifiers & Detergents, Volume 1, published by McCutcheon's Division of MC Publishing Company, 1997.

When used to increase the foam of an anionic surfactant, the carboxylated alkyl polyglycoside is added to a surfactant system comprised of one or more anionic surfactants, preferably in an aqueous system, in an amount effective to increase the foaming of the surfactant system to the desired degree. The amount of increased foaming will vary depending upon the nature of the anionic surfactant used or mixture of surfactants and the particular carboxylated alkyl polyglycoside used.

According to another aspect of the invention, there is provided a cleaning composition containing from about 5 to about 75% by weight and preferably from about 20 to about 35% by weight, and more preferably from about 25 to about 30% by weight of the combination of a carboxylated alkyl polyglycoside and an anionic surfactant, based on the weight of cleaning composition. The formulation of cleaning compositions may vary widely. It is well known that detergent and cleaning compositions contain surfactants and, in most cases, builders. While various surfactants, builders and additives may be employed in combination with the carboxylated alkyl polyglycoside, the basis of this aspect of the invention is the presence of the carboxylated alkyl polyglycoside in a cleaning composition, in the above-disclosed amounts.

The combination of a carboxylated alkyl polyglycoside with an anionic surfactant, according to the present invention, may also be employed to improve foaming in cleaning compositions and personal care products such as cosmetic and pharmaceutical formulations. Personal care products include, for example, hair shampoos, hair lotions, bubble baths, skin creams, lotions, and ointments. Cleaning compositions include shower gels, shampoos, dish washing detergents and fine fabric wash. Thus, according to another embodiment of the present invention, there is provided a surfactant composition containing the combination of a carboxylated alkyl polyglycoside and an anionic surfactant of the present invention in an amount of from about 0.1 to about 50% by weight, preferably from about 1 to about 25% by weight, and most preferably from about 2 to about 15% by weight, based on the weight of the surfactant composition.

Additional auxiliaries and additives which may also be employed in the compositions of the present invention include, but are not limited to, mild surfactants, oily substances, emulsifiers, superfatting agents, pearly luster waxes, stabilizers, consistency-imparting agents, thickeners, cationic polymers, silicone compounds, biogenic active ingredients, anti-dandruff agents, film-forming agents, preservatives, hydrotropes, solubilizers, UV light protection filters, insect repellents, artificial tanning agents, perfume oils, dyes, and the like.

The amount of auxiliaries and additives that may be employed can range from about 1 to about 50% by weight, and preferably from about 5 to about 40% by weight, based on the weight of the surfactant composition. The production of the surfactant composition may take place using any customary cold or hot processes.

The present invention will be better understood from the examples which follow, all of which are intended to be illustrative only, and are not meant to unduly limit the scope of the invention in any way.

EXAMPLES

The inverted cylinder test was used to show the foam increases that occur using a carboxylated alkyl polyglycoside surfactant. The carboxylated surfactant used in the examples was an ether carboxylated version of PLANTAREN® 1200 surfactant (a trademark of Henkel Corporation, Ambler Pa.) which is a C12–C16 alkyl polyglucoside with an average degree of polymerization of about 1.4. The alkyl polyglucoside ether carboxylate was mixed with various anionic surfactants in ratios of 100:0. 80:20, 60:40, 40:60, 20:80, and 0:100.

One hundred milliliters of the blend was placed in a 500 ml graduated cylinder. The cylinder was inverted at a rate of 20 times per minute. The foam and liquid was then read. The surfactant concentration of the liquid was 0.125%.

Figure 7:
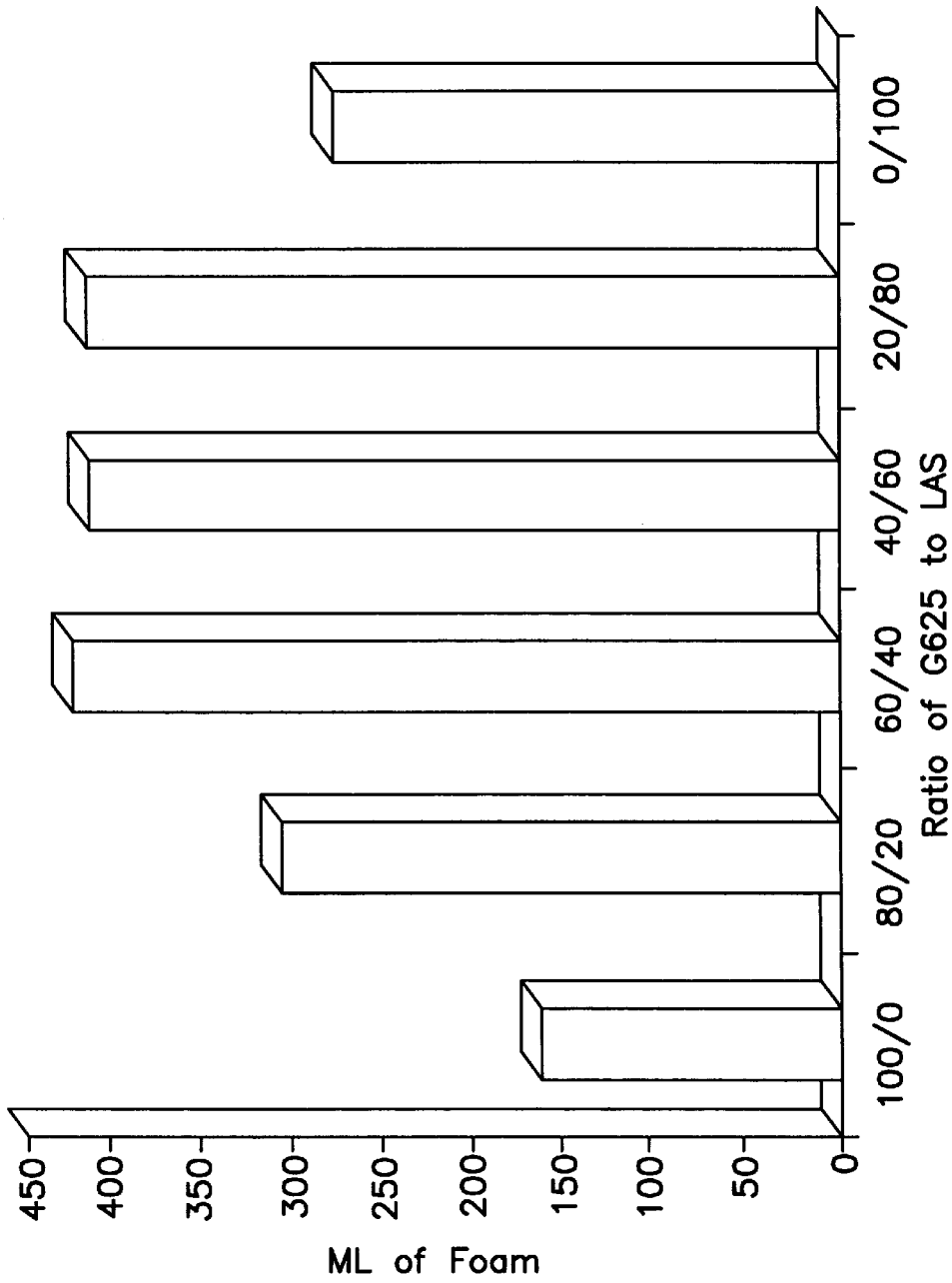
FIG. 7: Foam synergy of a nonionic alkyl polyglucoside surfactant, GLUCOPON® 625 (G625) Surfactant (Trademark of Henkel Corporation, Ambler, Pa.) with a C10–18 linear alkylbenzene sulfonate (LAS).
Figure 8:
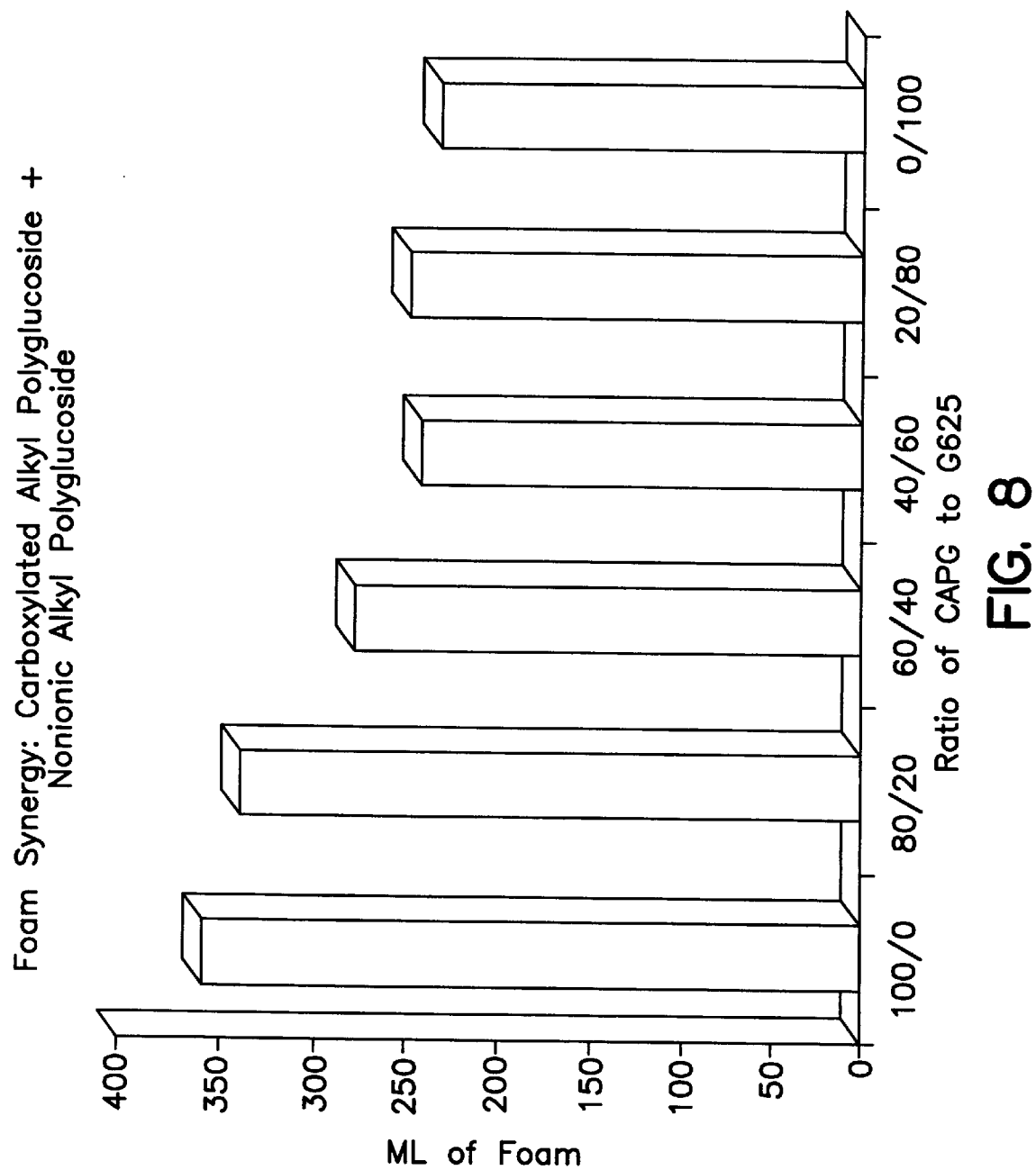
FIG. 8: Foam synergy of a carboxylated alkyl polyglycoside surfactant (CAPG) with a nonionic alkyl polyglycoside surfactant, GLUCOPON® 625 (G625).

The results of the experiments are shown in FIGS. 1–8. FIGS. 1–6 show the foam synergies of various anionic surfactants with the alkyl polyglucoside ether carboxylated surfactant. FIG. 7 shows the foam synergy of an alkyl polyglycoside surfactant, GLUCOPON® 625 with an anionic surfactant. FIG. 8 shows the foam synergy of a carboxylated alkyl polyglucoside surfactant with a nonionic alkyl polyglucoside surfactant.

EXAMPLE 2

A method of carboxylating an alkyl polyglycoside. Anhydrous alkylpolyglycoside is dissolved in a solvent such as DMF (dimethyl formamide). The anhydrous alkylpolyglycoside solution is added to an amount of succinic anhydride necessary to give a degree of substitution of 0.1 to 5. The succinic anhydride is also dissolved in a solvent such as DMF. The two solutions are combined at room temperature under a hydrogen blanket and mixed for an amount of time necessary to achieve the degree of substitution desired. Product is neutralized with a base. Solvent is evaporated.

EXAMPLE 3

The method of example 2 was performed as followed. 30 grams of an alkylpolyglucose having an average alkyl chain length of 11–13 and an average degree of substitution of 1.4–1.6 was dissolved in 30 gm of DMF. Succinic anhydride, 15.19 grams was dissolved in 60 gm of DMF. The two solutions were mixed together at room temperature for approximately 16 hours. The mixture was neutralized with NaOH.

After neutralization a precipitate formed. This seemed to correspond with a fraction that had a higher degree of substitution. When this method was used to make products with targeted lower degree of substitution no precipitation was observed.

What is claimed is:

1. A method of increasing foam of an anionic surfactant comprising combining an anionic surfactant with a carboxylated alkyl polyglycoside in a ratio by weight of from about 1:4 to about 4:1.

2. The method of claim 1 wherein the carboxylated alkyl polyglucoside is selected from the group consisting of the reaction product of an alkyl polyglycoside with an alpha- or 2-halocarboxylic acid, the reaction product of an alkyl polyglycoside with an alpha, beta-unsaturated carboxylic acid, the reaction product of an alkyl polyglycoside with a cyclic carboxylic acid anhydride and combinations thereof.

3. The method of claim 1 wherein the carboxylated alkyl polyglycoside is of formula I:

$$R_1O(R_2O)_b(Z)_aOCH_2COO^-X^+ \quad \text{I}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6; and X is an alkali metal ion.

4. The method of claim 3 wherein in formula I, $R_1$ is a monovalent organic radical having from 8 to 16 carbon atoms, b is zero, Z is a glucose residue and a is a number having a value of from about 1 to about 2.

5. The method of claim 3 wherein in formula I, $R_1$ is a monovalent organic radical having from 8 to 10 carbon atoms, b is zero, Z is a glucose residue and a is a number having a value of about 1.7.

6. The method of claim 3 wherein in formula I, $R_1$ is a monovalent organic radical having from 8 to 16 carbon atoms, b is zero, Z is a glucose residue and a is a number having a value of about 1.55.

7. The method of claim 3 wherein in formula I, $R_1$ is a monovalent organic radical having from 12 to 16 carbon atoms, b is zero, Z is a glucose residue and a is a number having a value of about 1.6.

8. The method of claim 3 wherein in formula I, $R_1$ is a monovalent organic radical having from 9 to 11 carbon atoms, b is zero, Z is a glucose residue and a is a number having a value of about 1.6.

9. The method of claim 3 wherein in formula I, $R_1$ is a monovalent organic radical having from 12 to 16 carbon atoms, b is zero, Z is a glucose residue and a is a number having a value of about 1.4.

10. The method of claim 3 wherein in formula I, $R_1$ is a monovalent organic radical having from 8 to 16 carbon atoms, b is zero, Z is a glucose residue and a is a number having a value of about 1.5.

11. The method of claim 3 wherein the anionic surfactant is selected from the group consisting of C8–C22 alkyl fatty acid salts of an alkali metal, alkaline earth metal, ammonium, alkyl substituted ammonium, alkanolammonium; sodium salts of tallow fatty acids, coconut fatty acids; alkali metal salts of organic sulfur reaction products having in their molecular structure an alkyl radical containing from about 8 to 22 carbon atoms and a radical selected from the group consisting of sulfonic and sulfuric acid ester radicals; organic phosphate esters and mixtures thereof.

12. The method of claim 4 wherein the anionic surfactant is selected from the group consisting of C8–C22 alkyl fatty acid salts of an alkali metal, alkaline earth metal, ammonium, alkyl substituted ammonium, alkanolammonium; sodium salts of tallow fatty acids, coconut fatty acids; alkali metal salts of organic sulfur reaction products having in their molecular structure an alkyl radical containing from about 8 to 22 carbon atoms and a radical selected from the group consisting of sulfonic and sulfuric acid ester radicals; organic phosphate esters and mixtures thereof.

13. An enhanced foaming composition comprising a surfactant having formula I:

$$R_1O(R_2O)_b(Z)_aOCH_2COO^-X^+ \quad \text{I}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6; and X is an alkali metal ion; and an anionic surfactant the surfactant having formula I and the anionic surfactant in a ratio by weight of from about 1:4 to about 4:1.

14. The product of the method of claim 1.

15. A cleaning composition comprising a mixture of an anionic surfactant and a carboxylated alkyl polyglycoside in a ratio by weight of from about 1:4 to about 4:1.

16. The cleaning composition of claim 15 wherein the mixture is present in the cleaning composition in an amount of from about 20 to about 35% by weight, based on the weight of the composition.

\* \* \* \* \*